(12) United States Patent
Rahn

(10) Patent No.: US 8,594,765 B2
(45) Date of Patent: Nov. 26, 2013

(54) METHOD FOR PROVIDING AN AID FOR USE IN THE THERAPEUTIC TREATMENT OF A SOMATIC SUBJECT

(75) Inventor: Norbert Rahn, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 173 days.

(21) Appl. No.: 13/197,234

(22) Filed: Aug. 3, 2011

(65) Prior Publication Data

US 2012/0046725 A1 Feb. 23, 2012

(30) Foreign Application Priority Data

Aug. 17, 2010 (DE) .......................... 10 2010 039 407

(51) Int. Cl.
*A61B 5/05* (2006.01)
(52) U.S. Cl.
USPC ........................ 600/407; 600/410; 600/437
(58) Field of Classification Search
USPC ................................................ 600/407–469
See application file for complete search history.

(56) References Cited

U.S. PATENT DOCUMENTS 7,333,643 B2 * 2/2008 Murphy et al. ................ 382/128
8,315,812 B2 * 11/2012 Taylor .............................. 702/19
8,315,813 B2 * 11/2012 Taylor et al. .................... 702/19
8,315,814 B2 * 11/2012 Taylor et al. .................... 702/19
8,321,150 B2 * 11/2012 Taylor .............................. 702/19
8,386,188 B2 * 2/2013 Taylor et al. .................... 702/19
2005/0187461 A1 * 8/2005 Murphy et al. ............... 600/416

FOREIGN PATENT DOCUMENTS

| DE | 102004044435 A1 | 3/2006 |
| DE | 102005035181 A1 | 3/2006 |
| DE | 102008014792 B3 | 6/2009 |
| DE | 102009046891 A1 | 5/2010 |
| EP | 2186491 A1 | 5/2010 |

OTHER PUBLICATIONS

F. Kari et al., "Fluss-sensitive 4D Magnetresonanztomographie", Zeitschrift für Herz-, Thorax- und Gefäßchirurgie vol. 21, No. 1 / Feb. 2007; Magazine; 2007, pp. 31-38.
Ansys Fluent oder Ansys CFD; Others; "Fluid Analysis Solutions" 12.1 Release Website: http://www.ansys.com/products/fluid-dynamics/cfd/, Retrieved: Mar. 30, 2010.

* cited by examiner

*Primary Examiner* — Sanjay Cattungal

(57) ABSTRACT

Blood flow turbulence or stationary blood can occur in vessels of the body, in particular following surgical interventions or minimally invasive interventional procedures, and this can lead to the formation of thrombi. A model of such vessels is obtained on the basis of a 3D image dataset, a simulation is then performed and a check carried out to determine whether turbulence or stationary blood can be demonstrated in the simulation. The model is then modified, successively where necessary, until the simulation reveals no more turbulence. Then, on the basis of the most recently modified model that results in no turbulence and no stationary blood, an aid is provided, in particular a specific aid such as e.g. a stent produced or a screen display presented.

17 Claims, 2 Drawing Sheets

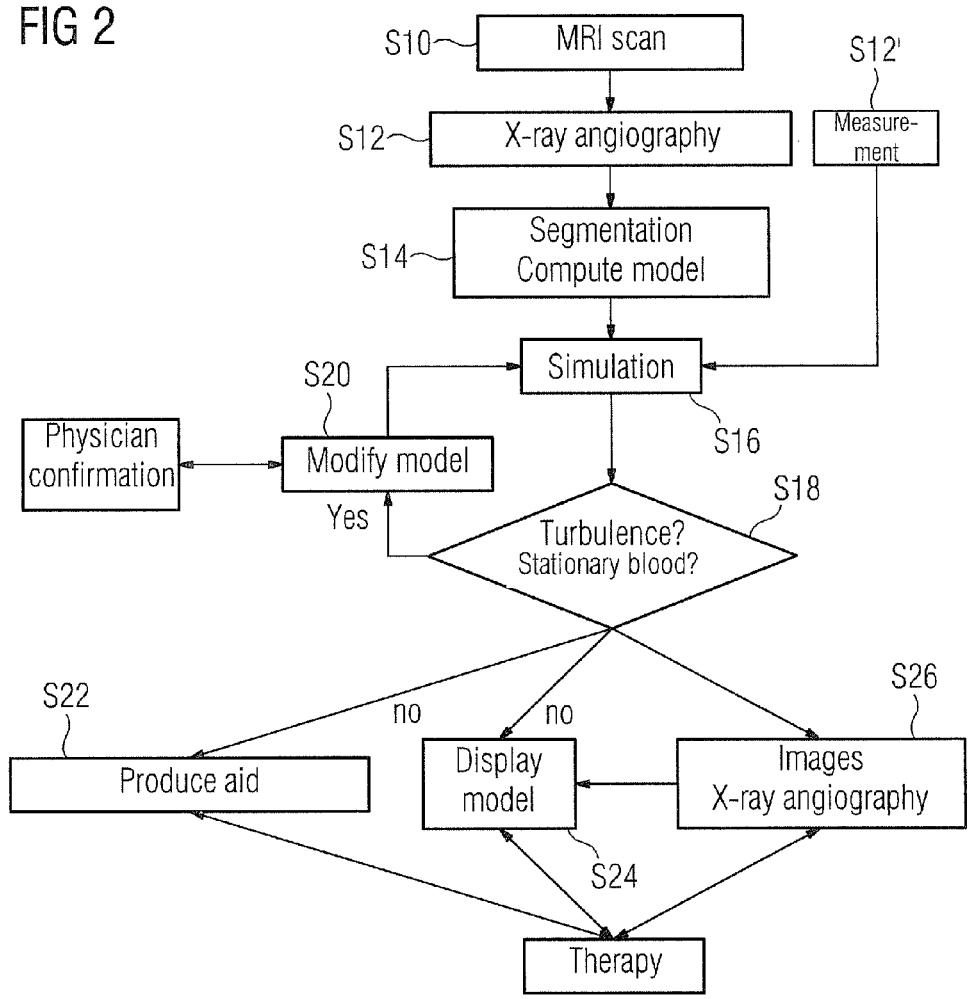

METHOD FOR PROVIDING AN AID FOR USE IN THE THERAPEUTIC TREATMENT OF A SOMATIC SUBJECT

CROSS REFERENCE TO RELATED APPLICATIONS

This application claims priority of German application No. 10 2010 039407.6 filed Aug. 17, 2010, which is incorporated by reference herein in its entirety.

FIELD OF THE INVENTION

The invention relates to a method for providing an aid for use in the therapeutic treatment of a somatic subject such as one or more blood vessels or an organ, in particular the heart.

BACKGROUND OF THE INVENTION

The physical structure of the body of a healthy human being ensures that as a general rule no thrombi occur. The occurrence of thrombi is promoted when turbulence in the bloodstream (vortex in the blood) occurs in the blood vessels or organs. Blood clots leading to a thrombus can also form in areas where the blood comes to a standstill.

Turbulence in the bloodstream occurs in particular in the wake of a human intervention into the structure of vessels or of the heart. Thus, in the case of congenital heart defects the structure of the ventricles of the heart and vessels (cardiovascular morphology) is modified for example by surgical interventions such as, say, the transplantation or occlusion of cardiac vessels or by minimally invasive interventional procedures such as, say, the placement of stents and balloon dilatation. Such changes naturally lead to a change in the flow conditions of the blood flow, and for precisely that reason turbulence can occur.

It would be desirable if such turbulence could be prevented as far as possible.

It is known from the article by F. Kari et al.: "Fluss-sensitive 4D Magnetresonanztomographie" ("*Flow-sensitive 4D magnetic resonance tomography*"), DGTHG, 2007, that a precisely detailed visualization of the morphology of the cardiovascular system is possible with the aid of modern-day magnetic resonance tomography. Blood flow rates can be measured by means of phase contrast methods. A detailed analysis of the 3D flow conditions is made possible through a combination of time-resolved, three-dimensional imaging and simultaneous acquisition of three-directional blood flow rates. In particular vortices can be visualized three-dimensionally.

Turbulence in the blood can also be detected with the aid of 4D ultrasound imaging (Doppler imaging).

A blood flow can also be simulated in 3D models. This is made possible for example by means of the software "ANSYS FLUENT" and "ANSYS CFD" of the company ANSYS, Inc., Canonsburg, Pa., U.S.A.

SUMMARY OF THE INVENTION

It is the object of the present invention to disclose a way in which the prevention of turbulence can be ensured.

The object is achieved by means of a method having the features recited in the claims.

The method according to the invention therefore serves to provide an aid for use in the therapeutic treatment of a somatic subject and comprises the following steps of:
a) acquiring a 3D image dataset of the subject to be treated,
b) processing the 3D image dataset in order to obtain a 3D model of the subject,
c) performing calculations for a simulation of blood flow through the subject corresponding to the 3D model,
d) checking whether the simulation demonstrates blood turbulence or stationary blood, and if yes:
e) modifying the 3D model,
f) performing calculations for a simulation of blood flow through the subject corresponding to the modified 3D model,
g) rechecking whether the simulation demonstrates blood turbulence or stationary blood, and
h) repeating steps e) to g) for as long as the check in step g) yields a non-negative result, i.e. for as long as no blood turbulence and no stationary blood are demonstrated, and when finally no more turbulence and no more stationary blood are demonstrated,
i) using the most recently modified model for providing the aid.

Within the scope of the invention there is therefore a direct relationship between the aid and the objective to be achieved, namely that no more turbulence and no more stationary blood should occur. Accordingly the aid can be implemented in a tailor-made design.

In a particularly preferred embodiment variant the aid includes an object that is to be introduced into the subject to be treated, said object being fashioned or manufactured in such a form (and at any event receiving a corresponding shape) that upon its being introduced into the subject it is to be possible to establish an actual state corresponding to the most recently modified model (i.e. said state can be produced if the model accurately replicates reality in a true-to-life manner).

In this context a stent in particular should be cited as a typical example in the treatment of vessels. Its shape can instantly determine how the vessel into which it has been introduced will subsequently appear. If the target specification for this appearance is given based on the modified model and the stent has been manufactured in accordance with said target specification, then it is ensured with a high degree of probability that following the treatment an actual appearance of the vessel is achieved which corresponds exactly to the target specification or at least ensures that no more turbulence and stationary blood will occur.

As an alternative to a stent, the aid can for example also comprise a balloon catheter, for its shape too can determine the subsequent shape of the dilated vessel to a certain extent.

In addition to a purely material aid, the aid can also consist in the provision of information. In particular it can include a screen display using the most recently modified model. If, namely, the treating physician is presented with a display representing the objective that he or she is intended to achieve, i.e. how the vessel or organ to be treated is subsequently to appear, then this simplifies the treatment for the treating physician.

This applies to a particular degree when further data is used in addition to the screen display, in which case in particular a simultaneous display is provided. For example, the type of screen display can comprise an overlaying of image data from at least two datasets, of which the precisely preferred one dataset is the dataset associated with the most recently modified model and the other dataset belongs to further image data. The further image data can be image data from a 3D rotation angiography scan, it can be 3D nuclear spin data (MR image data), or else it can be 2D or 3D ultrasound image data, possibly with Doppler information. In a possible treatment of the patient, image data can also be acquired during the treatment and overlaid with the image data associated with the most recently modified model, whereupon both "actual" and "ideal" can be seen in the overlay image. Apart from an overlay, other types of visualization can of course be used as well, in the simplest case two separate visualizations being provided immediately next to each other.

Preferably the aid, if it includes a screen display, additionally comprises an X-ray C-arm of an X-ray angiography device that is set to match the screen display, and by preference in addition an X-ray image of the subject taken with the X-ray C-arm in the thus set position. This is because it can be determined with the aid of the most recently modified model from which perspective the actual state of the patient subject to be treated can best be visualized so as to enable a direct comparison to be made with the most recently modified model or, as the case may be, so as to facilitate the treatment in accordance with the most recently modified model.

In the method according to the invention a check is preferably carried out before step a) with the aid of a magnetic resonance image to determine whether turbulence or stationary blood is occurring in the subject. This can be accomplished with the aid of flow-sensitive 4D magnetic resonance tomography in accordance with the methodology described in the above-cited article by F. Kari et al. Only if turbulence or stationary blood is actually identified in the subject are the steps of claim 1 then performed, in which case the 3D image dataset is preferably acquired with the aid of an X-ray angiography device in step a). Such a 3D image dataset in particular permits especially effective subsequent processing.

Step b) can in particular comprise what is termed segmentation: In segmentation, image processing techniques are applied so as to highlight structures having predetermined properties (which are chosen in particular so that the structures correspond to walls of the subject, in particular of a vessel) in the image. For example, in the simplest case a threshold criterion can be used in order to demarcate what belongs to the wall of a vessel, and what does not. Preferably the structures are assigned lattice sites in a space lattice. The 3D model is therefore provided as a lattice model, thereby simplifying a simulation.

In a preferred embodiment variant of the invention, measured values relating to pressure prevailing in the subject and/or to the mass flow of the blood flowing through the subject are acquired in addition in step a) and taken into account in steps c) and f). Incorporating such measured values helps increase the precision with which actual occurrences of blood turbulence or stationary blood can be demonstrated in a simulation. Within the scope of step f) it can where appropriate be taken into consideration how the measured value would change in the event of changes in the subject.

The modification of the 3D model is of course intended to simulate a target shape of the subject to be treated. During this process it may be helpful if the model is modified by means of a computer program programmed on the basis of many years of experience of treating professionals. Such a computer program can e.g. more accurately determine the effect of a stent at a specific point and then vary the effects by varying the notional shape of the stent.

It is equally well possible also for the modification to be effected based on an input received at a human-machine interface to a computer system in which the 3D model is made available. In the simplest case an operator for example can make a change in the 3D model by moving a vessel wall with the aid of a computer mouse.

BRIEF DESCRIPTION OF THE DRAWINGS

A preferred embodiment variant of the invention is described below with reference to the drawing, in which:

FIG. 2 is a flowchart serving to explain an embodiment variant of the method according to the invention.

DETAILED DESCRIPTION OF THE INVENTION

Figure 1:
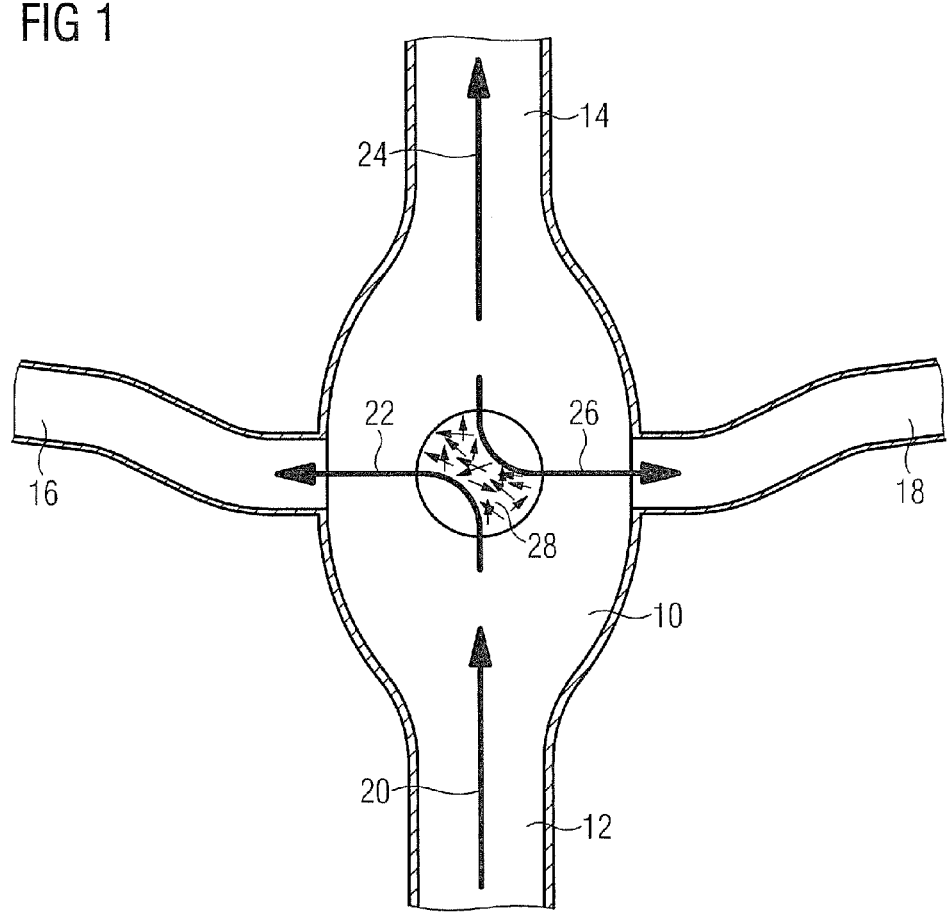
FIG. 1 is an illustration of the invention within the context of a Fontan operation depicting branches of the pulmonary artery connected to the right atrium of the heart.

The inferior vena cava 12 and the superior vena cava 14 open into the right atrium 10. In the present case the right-hand branch 16 of the pulmonary artery and the left-hand branch 18 of the pulmonary artery are to be connected to the right atrium of the heart 10 by means of an operation. Blood from the inferior vena cava flows as indicated by the arrow 20 into the right atrium of the heart 10 and then passes according to the arrow 22 into the left-hand branch of the pulmonary artery. Blood from the superior vena cava 14 flows as indicated by the arrow 24 into the right atrium of the heart 10 and then passes according to the arrow 26 into the right-hand branch 16 of the pulmonary artery. Blood flow turbulence (vortex in the blood) can occur in the central region 28 in the right atrium of the heart 10, and to some extent the blood can also come to a standstill here. There is an increased risk of formation of blood clots (thrombi) in this region.

A follow-up treatment after the operation is indicated here so that the turbulence can be prevented. In the method described below it is illustrated how a treating physician receives assistance in carrying out such a follow-up treatment for cases such as the exemplary scenario shown in FIG. 1.

The method according to the invention starts with step S10, a magnetic resonance tomography scan of a region of the body in which blood flow turbulence and stationary blood are to be expected. In the present case in particular a so-called flow-sensitive 4D magnetic resonance tomography method according to F. Kari et al. (cf. the above-cited article) is to be performed. Vortices can be detected here. If blood flow turbulence is detected, a transition is made to step S12: A 3D image dataset is acquired with the aid of an X-ray angiography device (in particular an X-ray C-arm device). Simultaneously, in step S12', the pressure in the vessel or organ of interest is measured with the aid of a catheter, as also, in addition, is the blood mass flow.

In the 3D image dataset, the vessel walls, in the exemplary scenario those of the inferior vena cava 14, the superior vena cava 16 and the pulmonary artery (branches 16 and 18) as well as the walls of the right atrium of the heart 12 are particularly readily identifiable in the 3D image data as a result of the fact that either particularly low or particularly high grayscale values have been assigned. By means of so-called segmentation, e.g. in particular by formation of threshold values, said walls of the vessels and chambers can be determined computationally. This enables a 3D model of the entire subject with right atrium of the heart 10 and vessels 12, 14, 16, 18 to be determined, e.g. a space lattice is defined, and it is specified in relation to the individual lattice points whether these are filled by a vessel or heart wall or not. In this way a 3D model of the subject is obtained in step S14.

In step S16 there then follows a simulation calculation in relation to the blood flow through the subject corresponding to the corresponding model. In step S18 a check is carried out to determine whether the simulation demonstrates turbulence or stationary blood. The evidence can be furnished on the basis of mathematical criteria in the computed data, or an operator can view a visual, in particular filmic, representation of the simulation and a make a corresponding input at a user interface (human-machine interface).

For as long as turbulence or stationary blood is identified in step S18, a branch is made to step S20: the model is modified. In particular the vessel walls are contracted or expanded, that is to say adjusted in any form, with the aim of achieving a target specification indicating how the subject of interest can be shaped in a treatment (or follow-up treatment). The modification of the model in step S20 can also be performed automatically by means of a computer program which, as a result of programming, takes into account experience gained in performing treatment. The model can also be modified on the basis of a user input. Where appropriate the user input can be made with the support of a computer program: it is conceivable for example for the user to choose one shape from a plurality of shapes for stents and for the computer program then to compute how the vessel would appear upon introduction of precisely the chosen stent into the vessel. When the model is modified according to step S20, an input by a physician can be received where appropriate to confirm that the target specification can actually be implemented.

Following step S20, another simulation is performed in step S16, and once again a branch is made to step S18 and a check carried out to verify whether turbulence or stationary blood is continuing to occur as previously. A return to step S20 is made repeatedly for as long as such turbulence or stationary blood can be demonstrated.

Once no further turbulence and no stationary blood occur, a branch can be made from step S18 to steps S22, S24 and S26. In step S22, an aid is produced in accordance with the model in the form which resulted in the last pass through step S20, i.e. the most recently modified model. If the vessel walls are therefore provided in any form as changed, a stent or a balloon catheter for example is produced to a certain extent made-to-measure for the patient. In this case the most recently modified model indicates how, upon introduction of the stent or dilatation of the balloon catheter, the previous vessel or organ is to appear subsequently.

The most recently modified model is displayed in step S24. Step S24 can be performed alternatively or in addition to step S22. By the most recently modified model being displayed it is possible for a treating physician to see how the subject of interest is to appear following its therapy. The physician is thus guided when carrying out his or her treatment.

Further images can be recorded in step S26, e.g. fluoroscopic images by means of X-ray angiography, etc. In this case an X-ray C-arm of the X-ray angiography device can be maneuvered into such a position that a particularly good comparison is made possible between the recently modified model and the actual state of the subject. The display of the model in step S24 can in this case be combined with a visualization of further image data, e.g. an overlay visualization can be provided based on a positionally and dimensionally correct assignment of the image data (a so-called registration in which a mapping rule is computed from mapping from a coordinate system associated with a first image dataset to a second coordinate system associated with a second image dataset). In addition to step S26, further steps performed in parallel are possible, e.g. ultrasound images can be recorded, etc.

Steps S22, S24 and S26 as well as possible further steps facilitate the therapy, though they themselves are not part of the same.

The invention claimed is:

1. A method for aiding a therapeutic treatment of a somatic subject of a patient, comprising:
    acquiring a 3D image dataset of the subject;
    processing the 3D image dataset to obtain a 3D model of the subject;
    calculating a simulation of a blood flow through the subject corresponding to the 3D model;
    checking whether the simulation demonstrating a blood flow turbulence or a stationary blood;
    modifying the 3D model if demonstrating the blood flow turbulence;
    recalculating a further simulation of the blood flow through the subject corresponding to the 3D model;
    rechecking whether the further simulation demonstrating the blood flow turbulence or the stationary blood;
    repeating the steps of modifying, recalculating and rechecking until yielding a non-negative result; and
    aiding the therapeutic treatment by using the 3D model last modified.

2. The method as claimed in claim 1, wherein an object is introduced into the subject for aiding the therapeutic treatment.

3. The method as claimed in claim 2, wherein the object upon being introduced into the subject establishes an actual state corresponding to the 3D model last modified.

4. The method as claimed in claim 3, wherein the object comprises a stent and/or a balloon catheter.

5. The method as claimed in claim 1, wherein the 3D model last modified is displayed in a screen for aiding the therapeutic treatment.

6. The method as claimed in claim 5, wherein further data is displayed in the screen.

7. The method as claimed in claim 6, wherein the further data comprises an overlaying of the 3D model last modified with another image data.

8. The method as claimed in claim 5, wherein a position of a C-arm of an X-ray angiography device is adjusted to match the displayed 3D model last modified.

9. The method as claimed in claim 8, wherein an X-ray image of the subject is taken using the X-ray angiography device in the adjusted position is displayed in the screen.

10. The method as claimed in claim 1, wherein a magnetic resonance image of the subject is taken prior to acquiring the 3D image dataset for determining whether the blood flow turbulence or the stationary blood is occurring in the subject.

11. The method as claimed in claim 1, wherein the processing step comprises highlight structures having predetermined properties, lattice sites in a space lattice.

12. The method as claimed in claim 11, wherein the structures comprise walls of the subject.

13. The method as claimed in claim 11, wherein the lattice sites are assigned to the structures.

14. The method as claimed in claim 1, wherein a pressure in the subject and/or a mass flow of a blood flowing through the subject is acquired and used in the steps of calculating and recalculating.

15. The method as claimed in claim 1, wherein the 3D model is automatically modified by a computer program.

16. The method as claimed in claim 1, wherein the 3D model is modified based on an input of a user interface to a computer system.

17. The method as claimed in claim 1, wherein the somatic subject comprises one or more blood vessels and/or a heart of the patient.

* * * * *